(12) United States Patent
Jost

(10) Patent No.: US 12,060,552 B2
(45) Date of Patent: Aug. 13, 2024

(54) METHOD AND APPARATUS FOR THE PURIFICATION OF EXTRA-CHROMOSOMAL NUCLEIC ACIDS SEQUENCES

(71) Applicant: KANEKA EUROGENTEC S.A., Seraing (BE)

(72) Inventor: Laurent Jost, Seraing (BE)

(73) Assignee: KANEKA EUROGENTEC S.A., Seraing (BE)

( * ) Notice: Subject to any disclaimer, the term of this patent is extended or adjusted under 35 U.S.C. 154(b) by 929 days.

(21) Appl. No.: 16/965,211

(22) PCT Filed: Jul. 4, 2019

(86) PCT No.: PCT/EP2019/067997
§ 371 (c)(1),
(2) Date: Jul. 27, 2020

(87) PCT Pub. No.: WO2020/011641
PCT Pub. Date: Jan. 16, 2020

(65) Prior Publication Data
US 2021/0062182 A1    Mar. 4, 2021

(30) Foreign Application Priority Data

Jul. 12, 2018 (EP) .................................... 18183258

(51) Int. Cl.
| | | |
|---|---|---|
| *C12N 15/10* | (2006.01) | |
| *B03D 1/14* | (2006.01) | |
| *B03D 1/24* | (2006.01) | |
| *C12M 1/00* | (2006.01) | |

(52) U.S. Cl.
CPC ....... *C12N 15/1003* (2013.01); *B03D 1/1431* (2013.01); *B03D 1/242* (2013.01); *C12M 47/06* (2013.01); *B03D 2203/003* (2013.01)

(58) Field of Classification Search
CPC .. C12N 15/1003; B03D 1/1431; B03D 1/242; B03D 2203/003; C12M 47/06
USPC ........................................................ 536/25.4
See application file for complete search history.

(56) References Cited

U.S. PATENT DOCUMENTS

| | | |
|---|---|---|
| 5,096,818 A | 3/1992 | DeBonville |
| 5,837,529 A | 11/1998 | Wan et al. |
| 7,314,746 B2 | 1/2008 | Au-Yeung et al. |
| 7,771,945 B2 | 8/2010 | Au-Yeung et al. |
| 7,842,481 B2 * | 11/2010 | Voss ......................... C12N 1/06 536/25.4 |
| 8,158,348 B2 | 4/2012 | Au-Yeung et al. |
| 8,276,888 B2 * | 10/2012 | Osborn ..................... C02F 1/78 261/115 |
| 2005/0014245 A1 | 1/2005 | Hebel et al. |
| 2011/0070638 A1 | 3/2011 | Au-Yeung |

FOREIGN PATENT DOCUMENTS

| | | |
|---|---|---|
| EP | 0811055 B1 | 6/2004 |
| EP | 1593741 B1 | 1/2009 |
| EP | 2153260 A1 | 2/2010 |
| WO | 9937750 A1 | 7/1999 |
| WO | 0005358 A1 | 2/2000 |
| WO | 2010136503 A1 | 12/2010 |

OTHER PUBLICATIONS

International Search Report and Written Opinion mailed Sep. 4, 2019, for International Application No. PCT/ EP/2019/067997 (17 pages).

* cited by examiner

*Primary Examiner* — Yih-Horng Shiao
(74) *Attorney, Agent, or Firm* — Fitch, Even, Tabin & Flannery LLP

(57) ABSTRACT

The present invention relates to a new apparatus and a new method for the purification and the recovery of extra-chromosomal nucleic acids sequence(s).

19 Claims, 6 Drawing Sheets

METHOD AND APPARATUS FOR THE PURIFICATION OF EXTRA-CHROMOSOMAL NUCLEIC ACIDS SEQUENCES

FIELD OF THE INVENTION

The present invention is in the field of biotechnology and concerns a method and an apparatus for the purification from contaminants and impurities of polynucleotide sequences, preferably extra-chromosomal nucleic acids sequence(s) selected from the group consisting of DNA plasmids, cosmids, BACs, YACS, MACs, mini-plasmids and mini-circles.

BACKGROUND OF THE INVENTION AND STATE OF THE ART

The purification of polynucleotides is generally obtained from host cells able to produce large quantities of these polynucleotides, possibly after genetic engineering.

It is known that a biomass of gram-negative bacteria, such as *Escherichia coli*, can be lysed and its nucleotides sequences of interest, especially extra-chromosomal nucleic acids sequences, separated from the bulk of genomic nucleic acids and proteins by successive purification steps including, but not limited to, a selective precipitation, a sedimentation, a filtration, and a specific retention on chromatographic columns.

However, depending on the protocol followed, these nucleic acids sequences of interest are combined with contaminants (or impurities), such as endotoxins, phenols, caesium chlorides, ethidium bromides, Triton®, bound proteins or other nucleic acids.

As highly-purified nucleotides sequences, especially extra-chromosomal nucleic acids sequences, are required for specific uses in laboratories or for clinical purposes, several attempts to reduce the amount of contaminants were proposed.

Generally, methods applied for their isolation involve a lysis step of cells with the addition of alkali, surfactant or enzymes, before a mixing with a neutralizing solution and eventually a precipitating solution to recover the extra-chromosomal sequence(s) in solution separated from precipitated contaminating cell components (genomic DNA, proteins and protein-nucleic acid complexes).

However, the use of alkaline solution, surfactants, heating step and/or long procedure(s) will degrade these nucleotides sequences. In addition, DNA molecules, including these extra-chromosomal nucleic acids sequence(s) are sensitive to mechanical stress. Furthermore, highly viscous solution may cause either local heterogeneities or require extensive mixing, both having the potential to degrade these nucleotides sequences. This is especially the case when concentrated chloride of divalent metals (such as $CaCl_2$) solutions are used.

It is known that batch wise methods present a risk of contamination and/or heterogeneity, especially at large scale.

The document WO2010/0136503 describes a method and an apparatus for an efficient purification of a DNA plasmid, wherein the precipitation of the DNA plasmid contaminants is obtained by a mixing of the disintegrated cells with a solution containing one or more salts, such as $CaCl_2$, in a passageway and by a subsequent separation of the precipitates from the solution through gravimetric decantation.

In this method and apparatus, an efficient mixing of the disintegrated cells and salts and the subsequent precipitation is obtained by the integration of means inducing a Venturi effect in the tubing elements. This Venturi effect is obtained by a reduction in the internal diameter in the tubing elements of about 40%. By the terms "inducing a Venturi effect", it is meant a turbulence in the flow obtained from the used system, wherein a fluid in laminar flow is forced to pass into reduced tubing in such an extent that the fluid has an increased speed and that a depression is caused just after the reduced diameter.

A Venturi effect created in the tubing elements causes an efficient mixing obtained without degrading the DNA plasmid and without creating high shearing forces in the liquid. Therefore, no degradation of DNA molecules is known to occur under heavy stirring or heavy shearing forces, which is necessary given the high viscosity of a 5 M $CaCl_2$ solution was observed in the described method. However, such method and apparatus requiring integration of means for inducing a Venturi effect, is dedicated to the production of few grams of plasmid and is not adequate for an upscaling of the production to larger amounts of extra-chromosomal nucleic acids sequences, i.e. kilograms up to tons.

The patent applications EP 811055-B1, WO99/37750 and WO00/05358 describe methods and apparatus of cellular lysis wherein a mixing of cells with a lysing solution is done into small tubings or static mixers having an adequate diameter length and preferably circular profile to obtain such lysis.

Furthermore, various means and steps are described in the scientific literature to improve the yield and efficiency of the purification steps of nucleic acids extracted from cells. For instance, the U.S. Pat. No. 5,096,818-B2 discloses a method for isolating and purifying nucleic acids sequences from a cells culture media by adding the lysing/denaturing agents and the deproteinating and/or neutralizing agents, without mixing, to resuspended cells, followed by a first centrifugation that partially pellets the cellular debris, and then mixing the solution to finalize the lysis, followed by a second centrifugation to completely pellet the cellular debris. This centrifugation method is not suitable for large scale processes due to equipment constraints leading to insufficient production yield.

The European patent EP 1 593 741-B1 discloses a method for producing a microbial clear lysate containing extra-chromosomal nucleic acids sequence(s) by mixing a suspension of microorganisms containing these nucleic acids sequences with a reaction buffer, reacting the mixture for a duration sufficient to break the microorganisms, transferring the obtained mixture into a vessel comprising a neutralizing buffer to form a precipitate with the contaminants to be removed, and generating gas bubbles by dispersing a gas through the bottom of the vessel to separate the precipitate from the lysate (liquid fraction that is not precipitated). As the neutralization buffer is not added continuously but the required, total quantity is present in the suspension from the beginning of the lysis, its concentration within the suspension (and therefore the neutralization power available in the suspension) changes with the process time, which induces process variability. Another restriction is that very large quantities of cells cannot be treated easily due to the system design and the batch processing.

The patents U.S. Pat. No. 8,158,348-B2; U.S. Pat. No. 7,771,945-B2 and U.S. Pat. No. 7,314,746-B2 disclose methods and apparatus for the purification of a DNA plasmid which comprises the addition of gas microbubbles with a lysis medium during lysis step of cells to improve the recovery of DNA plasmid of interest. As represented in the FIG. 5 of these US patents, the relative effect of different quantities of injected gas during lysis is not very efficient in view of the ultimate volume of resultant liquid phase obtained after separation and indicate that the amount of recovered liquid soluble fraction is only 60% or lower after a very long delay of treatment (about 16 hours).

AIMS OF THE INVENTION

The present invention is related to a method and an apparatus which do not present and solve the drawbacks of the methods and apparatus of the state of the art.

A preferred aim of the present invention is to obtain a cheap, robust and simplified method and apparatus for an efficient and rapid purification, especially through an improved separation (decantation or clarification) step, of one or more extra-chromosomal nucleic acids sequence(s) of interest from its impurities (or contaminants), especially a purification of large amounts of the extra-chromosomal nucleic acids sequence(s) of interest, in particular in amounts that are larger than the amount(s) obtained with the methods and apparatus of the state of the art.

A further aim of the invention is to obtain a new method and apparatus that allows a complete or almost complete recovery of the liquid clarified cells lysate containing the extra-chromosomal nucleic acids sequence(s) of interest, and wherein the obtained liquid clarified cells lysate comprises the extra-chromosomal nucleic acids sequence(s) of interest which is (are) less or is (are) not contaminated by its impurities (or contaminants) obtained from a precipitate layer.

SUMMARY OF THE INVENTION

In the method and apparatus according to the invention, by the terms "about" or "around", it is preferably meant a value plus or minus 20% or 10% (e.g. about 5 minutes means every value from 4 minutes and 30 seconds to 5 minutes and 30 seconds) above or lower the mentioned value.

The present method for obtaining by successive production and/or purification steps one or more extra-chromosomal nucleic acids sequence(s) of interest, preferably a DNA plasmid, preferably having a size lower than 30.000 bases (or base pairs), comprises (or consists of) the steps of:
a) optionally cultivating (preferably recombinant) hosts cells producing (involved in the synthesis of) the sequence(s) of interest and harvesting these cells containing the sequence(s) of interest, preferably cells containing this DNA plasmid of interest;
b) disintegrating these cells in a cells lysis unit, preferably through continuous introduction of cells into a passageway, this continuous introduction being a continuous feed of cells in a flow device, wherein preferably this disintegration is obtained through addition of an (alkaline) lysis medium to the cells in the cells lysis unit;
c) neutralizing the lysed cells (comprising the extra-chromosomal nucleic acids sequence(s) of interest) in a neutralization unit, by means of a neutralization solution, this neutralization solution being preferably added and being preferably composed of an acetic acid/acetate composition, to produce a cells lysate mixture comprising a soluble fraction (comprising the extra-chromosomal nucleic acids sequence(s) of interest, especially the DNA plasmid of interest) and a precipitate, this precipitate comprising contaminants and/or impurities of the sequence(s) of interest;
d) optionally (further) precipitating these contaminants and/or impurities of the extra-chromosomal nucleic acids sequence(s) of interest, especially of the DNA plasmid of interest, by mixing the cells lysate mixture (obtained from step c)), to advantageously purify this mixture. This (further) precipitation is performed by adding one or more, preferably hydrated, salt(s) in a continuous way to the, preferably disintegrated cells lysate mixture, in a solution at a concentration comprised between (about) 2M and (about) 6M, wherein the salt(s) is (are) selected from the group consisting of (comprising of) (preferably hydrated) $CaCl_2$, (preferably hydrated) $MgCl_2$, (preferably hydrated) $ZnCl_2$, (preferably hydrated) $SrCl_2$, (preferably hydrated) $BaCl_2$, or (less preferably) other (preferably hydrated) salt(s), such as LiCl, ammonium acetate, ammonium sulfate, sodium sulfate or magnesium sulfate, wherein the preferred salts are (preferably hydrated) $CaCl_2$ and/or (preferably hydrated) $MgCl_2$;
e) collecting the cells lysate mixture obtained from step c) or from step d) in a separation (decantation or clarification) tank;
f) separating (decanting or clarifying) the soluble fraction (comprising the extra-chromosomal nucleic acids sequence(s) of interest, especially the DNA plasmid of interest), from the precipitate (comprising contaminants or impurities) contained in the cells lysate mixture; this separation step preferably having a duration comprised between (about) 5 minutes and a few hours; more preferably comprised between (about) 15 minutes and (about) 2 hours. This separation step is advantageously performed in a tank or reservoir, called the separation (decantation or clarification) tank;
g) recovering from the separation tank, preferably by a pumping out, of the separated soluble fraction, comprising the extra-chromosomal nucleic acids sequence(s) of interest, especially the DNA plasmid of interest, present in this cells lysate mixture from this separation tank;
h) optionally performing one or more further separation step(s), decantation step(s) and/or filtration step(s) of the obtained soluble fraction upon one or more filter(s) having a pore size comprised between (about) 0.2 μm and (about) 20 μm, preferably followed by an ultra-filtration step upon an (about) 30 kDa membrane to (about) 500 kDa membrane, preferably between (about) 50 and (about) 250 kDa, more preferably between (about) 50 and (about) 100 kDa to obtain a first membrane retentate comprising the extra-chromosomal nucleic acids sequence(s) of interest, preferably the DNA plasmid of interest;
i) optionally performing a (polishing step) chromatography of the soluble fraction from step g) or of the first membrane retentate from step h), comprising the recovered extra-chromosomal nucleic acids sequences(s), preferably the DNA plasmid of interest, this chromatography step optionally comprising a washing sub-step to obtain a chromatography eluate;
j) optionally performing an ultrafiltration of the chromatography eluate from step i) upon an (about) 3 kDa to (about) 100 kDa membrane and collecting an obtained second retentate; and optionally performing a (yet even further) filtration of the second retentate upon an (about) 0.2 μm membrane to recover and collect in a filtrate, the extra-chromosomal nucleic acids sequence(s) of interest, preferably the DNA plasmid of interest, which is purified from its impurities (or contaminants).

By the terms "soluble fraction" (e.g. of the cells lysate), it is meant the liquid and soluble portion of a cells lysate mixture recovered by the method and apparatus of the invention, wherein this soluble fraction can be separated, decanted or clarified from a precipitate layer, which may comprise flocs floating in and above the liquid lysate mixture and wherein this precipitate layer may comprise or contain impurities (or contaminants) of the extra-chromosomal nucleic acids sequence(s) of interest to be recovered and purified. Hereafter, this obtained soluble fraction after separation, decantation and/or clarification is also called "the clarified phase". The separation step, i.e. the decantation step and/or clarification step, is preferably based upon a classic continuous process step, but that can be also performed according to a batch process instead of adding a continuous supply of feeding material.

By the term "extra-chromosomal nucleic acids sequence(s)", it is meant any nucleotide sequence of more than 50 bases (base pair). More preferably, this extrachromosomal nucleic acids sequence is selected from the group comprising of (consisting of) DNA plasmids, cosmids, BACSs, YACs, MACs, mini-plasmids and mini-circles, preferably a (DNA) plasmid, such as a (DNA) plasmid of a size smaller than 30 000 base pair.

According to the present invention, the separation step f) comprises at least one injection of a liquid aqueous medium comprising a dissolved gas into the cells lysate mixture contained in a separation (decantation or clarification) tank. This injection is not done during lysis of the cells nor during neutralisation of the lysed cells. Said liquid aqueous medium can be obtained by dissolving a gas in the liquid aqueous medium at an elevated pressure. It has surprisingly been found that the injection of a liquid aqueous medium comprising a sufficient amount of dissolved gas into the cells lysate mixture improves the yield of the separation (decantation or clarification) step between the soluble fraction comprising the extra-chromosomal nucleic acids sequence of interest and the precipitate, this separation step being performed in the above-mentioned separation tank. The improved separation yield significantly improves the quantity of recovered soluble fraction, in particular of recovered nucleic acids sequence(s) of interest. In the absence of said injection, the layer of precipitates remains immersed in the soluble fraction, entrapping a significant volume of this soluble fraction which is lost during the recovery step g). The injection realises the floating of the precipitates' layer on top of the soluble fraction because the spaces between the precipitate particles are filled with gas instead of (liquid) soluble fraction.

The liquid aqueous medium comprising the sufficient amount of the dissolved gas is advantageously obtained by dissolving the gas, preferably a gas selected from the group consisting of air, $CO_2$, oxygen, ozone, nitrogen or a mixture thereof, into a liquid aqueous medium, such as water. Preferably, this gas is dissolved in the liquid aqueous medium by means of bubbling. Advantageously, this dissolution is performed at a pressure above atmospheric pressure, such as a pressure of at least 1 barg, preferably between (about) 2 barg and (about) 50 barg, preferably between (about) 3 barg and (about) 25 barg, preferably between (about) 4 barg and (about) 15 barg. By so doing, a higher concentration of dissolved gas in the liquid aqueous medium can be obtained (Henry's law). The concentration of the dissolved gas in the liquid aqueous medium advantageously approximates the saturation concentration, e.g. the concentration of the dissolved gas in the liquid aqueous medium amounts to at least 50% of the saturation concentration at the indicated pressures, advantageously at least 60%, at least 70%, at least 80%, at least 90% of the saturation concentration. Advantageously, the liquid aqueous medium is saturated with the dissolved gas. The liquid aqueous medium is preferably saturated in gas at a pressure higher than (about) 2 barg, preferably comprised between (about) 2 barg and (about) 50 barg, more preferably between (about) 3 barg and (about) 25 barg. Advantageously, the volume amount of the liquid aqueous medium comprising the dissolved gas injected in the cells lysate mixture compared to the volume of the cells lysate mixture being treated (e.g. total volume of the cells lysate mixture in the tank), is comprised between (about) 0.2% v/v and (about) 25% v/v, preferably between (about) 0.5% v/v and (about) 15%, more preferably between (about) 1% v/v and (about) 10%, injected once or several times.

Preferably, the liquid aqueous medium comprising the dissolved gas is prepared into a reservoir or tank prior to injection of the liquid aqueous medium comprising the dissolved gas into the cells lysate mixture.

Advantageously, the liquid aqueous medium comprising the dissolved gas is injected at a pressure above atmospheric pressure in the cells lysate mixture, the latter being advantageously at a pressure around atmospheric pressure. Advantageously, this liquid aqueous medium is injected at substantially a same pressure as the pressure at which the gas is dissolved. Preferable injection pressure is at least (about) 2 barg, preferably between (about) 3 barg and (about) 50 barg, preferably between (about) 4 barg and (about) 15 barg. The liquid aqueous medium is advantageously injected in the cells lysate mixture intermittently. This means that a static rest period between two consecutive injection periods has advantageously at least a duration equal to the duration of the injection period prior to and after this static rest period. By way of example, a time period during which injection takes place (injection period) is between (about) seconds and (about) 10 minutes, more preferably of (about) 5 seconds and (about) 5 minutes. The static rest period between two consecutive injection periods is advantageously between (about) 5 seconds and (about) 10 minutes, advantageously at least equal to the duration of the injection period.

According to the invention, the injection of the liquid aqueous medium comprising a dissolved gas in the cell lysate mixture present in the separation (decantation or clarification) tank may be a single injection or a series of successive injection(s) injected intermittently. An intermittent injection of the liquid aqueous medium comprising the dissolved gas followed by a static rest period allows the precipitate to raise and the soluble fraction to clarify during the static rest time. At the same time, gas bubbles replace the soluble fraction entrapped within the flocs of the precipitate layer, leading to the floating of the precipitate layer on top of the soluble fraction instead of the precipitate being immersed in the soluble fraction. As a result, a larger volume of the soluble fraction can be recovered.

The host cells used in the method and integrated in the apparatus according to the invention are prokaryotic cells, such as bacteria, especially *E. coli* cells.

Preferably, in the method according to the invention, step b) comprises a mixing of the cells with the added (alkaline) lysis medium. Preferably, the mixing is done into a static mixer, this static mixer preferably comprising at least 6 mixing elements, preferably between 12 mixing elements and 24 mixing elements, more preferably 18 mixing elements. Preferably, the mixing linear speed is equal to or higher than 150 cm/min; preferably comprised between (about) 150 cm/min and (about) 2000 cm/min, more preferably comprised between (about) 500 cm/min and (about) 1500 cm/min.

Preferably, in the method according to the invention, step c) comprises a mixing of the cells lysate mixture with the neutralization solution. Preferably, the mixing is done into a static mixer, this static mixer preferably comprising at least 4 mixing elements, preferably between 6 and 16 mixing elements, more preferably 10 mixing elements. Preferably, the mixing linear speed is equal to or higher than 100 cm/min, preferably comprised between (about) 100 cm/min and (about) 2000 cm/min, more preferably comprised between (about) 340 cm/min and (about) 1025 cm/min.

Preferably, in the method according to the invention, step d) comprises a mixing of the cells lysate mixture obtained from step c) with the salt(s). Preferably, the mixing is done into a static mixer, this static mixer preferably comprising at least 2 mixing elements, preferably between 2 and 18 mixing elements, more preferably 4 mixing elements. Preferably, the mixing linear speed is equal to or higher than 100 cm/min, preferably comprised between (about) 100 cm/min and (about) 1500 cm/min, more preferably between (about) 400 cm/min and (about) 1200 cm/min.

In the method and apparatus of the invention, the cells are preferably maintained in a suspension and disintegrated by an addition of a (alkaline) lysis medium.

According to the invention, the lysis medium to disintegrate cells may be an alkaline solution having a pH comprised between (about) 11 and (about) 12.5, preferably a pH comprised between (about) 12 and (about) 12.5. The lysis medium may comprise a sufficient amount of one or more detergent(s).

In the method and apparatus according to the invention, the (alkaline) lysis medium may be obtained by mixing of at least a sufficient amount of NaOH with a sufficient amount at least one detergent. In the method and apparatus according to the invention, sufficient amounts of NaOH and detergent are selected by the skilled person according to the amount(s) of cells that need to be lysed. More preferably, the mixing may be performed by introduction of sufficient amounts of each reactive product solution (NaOH and the at least one detergent) into a static mixer, and mixing the components to form a (alkaline) lysis medium prior to addition of this (alkaline) lysis medium to the cells. Said static mixer preferably comprises at least at least 6 mixing elements, preferably between 12 and 24 mixing elements, more preferably 18 mixing elements. Preferably, the mixing linear speed is equal to or higher than 100 cm/min.

The (alkaline) lysis medium may comprise between (about) 0.01% and (about) 5%, preferably between (about) 0.1% and (about) 3%, more preferably between (about) 0.5% and (about) 3% (w:v) of one or more detergent(s). Preferably, the detergent is selected from the group consisting of Sodium Dodecyl Sulfate (SDS), Sodium Deoxycholate, Triton® X-100, Triton® X-114, Nonidet® P-40, Octylglucoside, Brij® 35, Brij® 56, Tween® 20, CHAPS(3-[(3-Cholamidopropyl)dimethylammonio]-1-propanesulfonate), or a mixture thereof.

Advantageously, in the disintegration step of the process (step b)), the cells are brought in suspension with the (alkaline) lysis medium. Preferably, the optimal contact time between the cells and the (alkaline) lysis medium is comprised between (about) 15 seconds and (about) minutes, preferably between (about) 0.5 minutes and (about) 5 minutes, more preferably (about) 2 minutes.

Preferably, the neutralization solution is an acetic acid/acetate solution having a pH comprised between (about) 5.0 and (about) 6.0, preferably of (about) 5.5. Preferably, the neutralization solution has a concentration of about 3 M (mol/l) of acetate and about 15% (v:v) of acetic acid.

Preferably, the neutralization solution, in particular the above-mentioned acetic acid/acetate solution, is chilled from room temperature to a temperature comprised between (about) 2° C. and (about) 8° C., preferably of (about) 4° C. This step is obtained by method well known by the skilled person in the art, preferably by storing the buffer in a cold room for a sufficient amount of time or by using an adequate cryostat connected to a heat exchanger surrounding the tubing element carrying the neutralization solution.

Advantageously, the optimal contact time of the lysed cells, comprising the extra-chromosomal nucleic acids sequence(s) of interest, and the neutralization solution is comprised between (about) 15 seconds and (about) 5 minutes, preferably between (about) 30 seconds and (about) 2 minutes, more preferably of (about) 1 minute.

Advantageously, the optimal contact time of the neutralized lysate and the precipitation solution is higher than 1 minute, this period being suitable for obtaining the required precipitation.

Advantageously, the optimal time of the separation (decantation or clarification) of step f) of the method according to the invention, is comprised between (about) 5 minutes and several hours, preferably between (about) 15 minutes and (about) 2 hours.

The method of the invention may optionally comprise a preliminary step between step a) and step b) comprising (or consisting of) the addition of a sufficient amount of RNase to the suspension of the (entire) cells comprising the extra-chromosomal nucleic acids sequence(s) of interest. The amount of RNase added is defined by the skilled person according to the type and amount of sequence(s) of interest to be purified and this RNase treatment is especially useful for a purification of plasmid DNA having a size inferior to 3000 bases (base pairs).

The preferred added hydrated salt of the method according to the invention is $CaCl_2.5H_2O$ which is added at a concentration comprised between (about) 2 M and (about) 6 M, preferably at a concentration of about 5 M.

In the method or apparatus of the invention, the continuous process or the continuous addition steps are performed via an opening and closing of inlets/outlets, pumps or valves and these pumps outputs are advantageously controlled by weighing the tanks, reservoirs, vials or recipients of the feeding solutions of the invention or by integration of flowmeters to the tubing(s) connecting these tanks.

In the method and apparatus of the invention, the filtration step is done on depth filters or on surface filters.

The chromatography step (step i)) optionally present in the method of the invention comprises (or consists of) one or more classical purification steps well known by the person skilled in the art.

Optionally, after this washing sub-step and prior to the elution sub-step, another washing sub-step may be performed with the same solution supplemented with one or more neutral detergent(s). Preferably, this neutral detergent is selected from the group consisting of Triton® X-100, Triton® X-114, Tween® 20, Nonidet® P-40, octylglucoside, Brij® 35, Brij® 56, or a mixture thereof. Preferably, said neutral detergent is present in the solution at (about) 0.1% to (about) 1%. This optional second washing sub-step may be followed by a further washing sub-step and this further sub-step preferably being performed without any neutral detergent being present.

The method and the apparatus of the invention allow the production and purification of large amounts of extra-chromosomal nucleic acids sequence(s) of interest, from less than one gram to hundreds of grams, kilograms, up to tons. However, in the process according to the invention the optional precipitation step (step d)) may be replaced by others purification steps before or after steps h) to j) to obtain the extra-chromosomal nucleic acids sequence(s) of interest of desired purity.

The invention also relates to an apparatus for carrying out the method according to the present invention. The apparatus of the present invention comprises (or consists of) means for obtaining a continuous flow, such as circular tubes or tubing elements, possibly connected to suitable tanks, reservoir(s), vials or recipient(s), and having inlet or opening means and outlet or exit means.

Advantageously, the tubing(s) of the apparatus are in accordance to the requirements for use in human medicine, especially with Pharma quality, and preferably are non-leachable and are linked through "Y-type connections".

The apparatus of the present invention comprises or preferably consists of:
- a preparation unit comprising one or more tanks containing compounds of a (alkaline) lysis medium, the tank(s) comprising one or more outlets the tank(s) being fluidly connected, preferably via one or more tubing(s), to the an inlet of a cells lysis unit, this inlet preferably being distinct from the inlet for the introduction of the cells from the cells suspension tank to the cells lysis unit,
- a cells lysis unit comprising a cells suspension tank containing cells with the extra-chromosomal nucleic acids sequence(s) of interest, the cells lysis unit comprising at least one inlet being fluidly connected, preferably via one or more tubing(s), to the cells suspension tank and to the outlet(s) of the preparation unit, further comprising at least one outlet being fluidly connected, preferably via one or more tubing(s), to the inlet(s) of a neutralization unit,
- a neutralization unit comprising a neutralization medium tank, at least one inlet and at least one outlet or exit, the inlet being in fluid connection, preferably via one or more tubing(s), with the neutralization medium tank and to the outlet(s) or exit(s) of the cells lysis unit, and the outlet(s) being fluidly connected to the inlet(s) of a separation (decantation or clarification) unit, or to an optional precipitation unit,
- optionally a precipitation unit comprising at least one inlet, at least one outlet or exit and a tank containing a solution of salts, the inlet(s) being in fluid connection, preferably via one or more tubing(s), with the tank containing a solution of salts and to the outlet(s) or exit(s) of the neutralization unit, and the outlet being fluidly connected, preferably via one or more tubing(s), to the inlet of the separation unit,
- a separation (decantation or clarification) unit comprising a separation (decantation or clarification) tank for a cells lysate mixture, having at least one inlet and at least one outlet, the inlet(s) fluidly connected to the outlet of the neutralization unit, or as the case may be, of the precipitation unit, the separation tank preferably comprising means for recovering the soluble fraction comprising the extra-chromosomal nucleic acids sequence(s) of interest from the cells lysate mixture, and
- an injection unit, in particular a floatation unit, comprising means for dissolving a gas in a liquid aqueous medium at a pressure higher than atmospheric pressure and means for injecting the liquid aqueous medium comprising a dissolved gas into the separation tank.

Preferably, the liquid aqueous medium is water and this liquid aqueous medium is advantageously saturated with a dissolved gas, this gas preferably being air, $CO_2$, $N_2$, $O_2$, ozone or a mixture thereof. More preferably, means for injecting the liquid aqueous medium comprising a dissolved gas into the separation tank comprises at least one injection pipe having an exit, preferably an exit nozzle oriented towards the bottom surface of the separation (decantation or clarification) tank. Preferably, the exit, preferably the exit nozzle, is disposed in the separation tank at a height, measured from the tank bottom surface, comprised between (about) 1/6 and (about) 5/6 of the total height of the tank, more preferably between (about) 1/4 and (about) 3/4 of the total height of the tank. This position advantageously avoids the resuspension of the precipitated contaminants and impurities that already are being separated.

Preferably, the means for dissolving a gas in a liquid aqueous medium comprises a liquid aqueous medium tank, preferably a water tank, and a bubbling device. This bubbling device preferably comprises a tubing, such as a pipe, connected to a gas container and preferably, a flowmeter is also connected to the tubing, and a pump is fluidly connected between the tubing and this gas container. The bubbling device provided controlled bubbling of the gas from the gas container into the liquid aqueous medium to obtain a liquid aqueous medium comprising a dissolved gas. Preferably, this bubbling device is configured to inject gas into the liquid aqueous medium tank at a pressure higher than or equal to 1 barg, preferably between 2 barg and 50 barg, preferably between 3 barg and 25 barg and advantageously in a volume comprised between (about) 5% and (about) 20% v/v compared to the volume of cells lysate mixture to treat.

In the apparatus according to the invention, the ratio between the liquid aqueous medium injection pipe internal diameter and its exit nozzle diameter may be (about) 1 or near the value of 1, but is preferably higher than (about) 3, more preferably higher than (about) 5, but preferably lower than 50. This specific injection pipe and nozzle combination ensures that the pressure inside the injection pipe does not drop below 90% of the initial value during injection of the liquid aqueous medium comprising the dissolved gas. This prevents an early degassing within the injection pipe instead of inside the cells lysate mixture, and improves the quality and quantity of purification. After injection of the liquid aqueous medium comprising a dissolved gas into the separation tank which is kept at atmospheric pressure, the liquid aqueous medium loses its dissolved gas, which generates in the cells lysate mixture (a fog of) (micro)bubbles having an average diameter smaller than or equal to 1.5 mm, preferably smaller than or equal to 1 mm or even smaller than or equal to 0.5 mm.

In the apparatus according to the invention, the injection pipe of the injection unit is separated from the inlet whereto the tubing between the separation unit or tank and the outlet(s) of the neutralization unit or the precipitation unit. Consequently, the aqueous liquid medium comprising a dissolved gas is injected into the separation tank via a separate inlet or tubing than the inlet for the cells lysate mixture.

The apparatus according to the invention may further include either known mixing elements, such as means generating a Venturi effect (i.e. as described in the international patent application WO2010/0136503 described herein by reference), optionally combined with one or more static mixer(s) for the efficient mixing of the fluids.

In the apparatus according to the invention, the preparation unit comprises either a single tank containing the lysis medium or two or more separated tanks containing its different components, the tank(s) are connected to the cells lysis unit by a first (set of) tubing(s), via one (or several) pump(s), a first static mixer, preferably comprising at least 6 mixing elements, this first static mixer having an inlet and an outlet or exit, wherein this inlet being connected to the tubing(s) coming from the pump(s) of the (alkaline) lysis medium or its separated components, and wherein the outlet or exit being connected, via a second tubing or more tubings, to the cells lysis unit. The size of the first static mixer (i.e. number of introduced mixing elements, as well as the diameter and the length of this first static mixer and the pump(s) output(s) are selected to allow a mixing linear speed of the introduced elements into the first static mixer, that is preferably higher than 100 cm/min.

The apparatus according to the invention may also comprise a cells lysis unit made of a second static mixer, preferably a second static mixer comprising between 12 and 24 mixing elements, preferably 18 mixing elements, this second static mixer having an inlet and an outlet or exit, the inlet being connected by the second tubing(s) to the outlet of the preparation unit and being connected via a third tubing or more tubings and a pump to the outlet of the cells suspension tank containing the cells suspension, and the outlet or exit of the second static mixer being connected to a fourth tubing or more tubings. The size of the second static mixer and the pumps outputs are selected to allow a mixing linear speed of the introduced solutions into the second static mixer that is comprised between (about) 1000 cm/min and (about) 1500 cm/min.

The apparatus according to the invention may further comprise a third static mixer, preferably a third static mixer comprising between 6 mixing elements and 16 mixing elements, preferably 10 mixing elements, this third static mixer having an inlet and an outlet or exit, the inlet being connected to a fourth tubing coming from the outlet of the cells lysis unit and being connected, via a fifth tubing and a pump to a neutralization medium tank, the outlet or exit of the third static mixer being connected to a sixth tubing or more tubings. The size of the third static mixer and the pumps outputs are selected to allow a mixing linear speed of the introduced solutions into the third static mixer that is preferably comprised between (about) 340 cm/min and (about) 1025 cm/min.

The apparatus according to the invention may further comprise a fourth static mixer, preferably a fourth static mixer comprising between 4 and 18 mixing elements, this fourth static mixer having an inlet and an outlet or exit, the inlet being connected to a sixth tubing coming from the neutralization unit and connected via a seventh tubing and a pump, to a tank containing a solution of (divalent) salts, and wherein the outlet or exit is connected via an eighth tubing to a separation (or decantation) tank. The size of the fourth static mixer and the pumps outputs are selected to allow a mixing linear speed of the introduced solutions into the fourth static mixer that is preferably comprised between (about) 400 cm/min and (about) 1200 cm/min.

The position of the pumps as represented in the figures also improves the treatment efficiency, because the pumps respective position as represented can advantageously allow a pushing (the flow) of fluids in the tubing(s), instead of a pulling of fluids present in these tubing(s), meaning that the treated product is not impacted by the shearing forces occurring in the pumps heads that could damage it and lower its quality.

Preferably, the apparatus of the invention further comprises means to weight the so called feeding solutions (i.e. the neutralization solution, lysis solution, . . . ) present in the different tanks, reservoirs, bags or recipients and/or comprises one or more flowmeter(s), for controlling the introduction of the different media or cells or cells fractions in the tubing(s). This means that the method of the invention may comprises steps that are performed continuously and steps that are performed in a batch after batch sequence. Preferably, the neutralization step is performed in a batch after batch sequence.

An alternative to the method or apparatus of the invention concerns the described method and apparatus that includes the described separation step and separation unit without injection of a liquid aqueous medium comprising dissolved gas and without the injection unit to inject a liquid aqueous medium comprising dissolved gas, but that will include together with the above described technical features, one or more of the above described static mixer(s) and one or more or all the mixing step(s) comprising the use of one or more of the static mixer(s).

The method and apparatus according to the present invention are described with reference to the enclosed figures in the following detailed description presented as a non-limiting preferred embodiment.

SHORT DESCRIPTION OF THE FIGURES

DETAILED DESCRIPTION OF THE INVENTION

Figure 1:
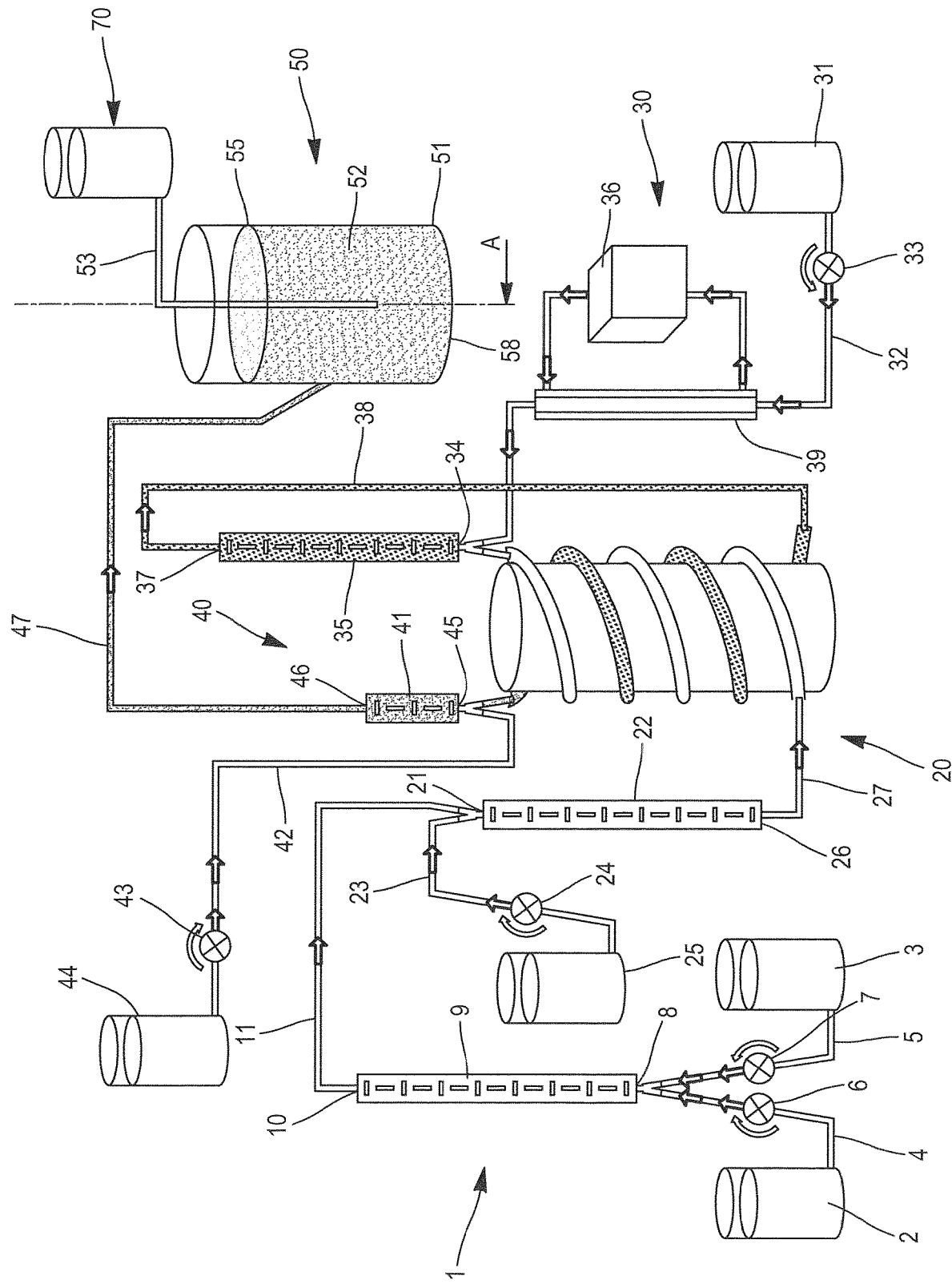
FIG. 1 represents schematically the apparatus of the invention.

The FIG. 1 illustrates the apparatus allowing to carry-out steps of the method of the present invention, being a pipe or tube of several meters long, made of several tubes or tubing elements having circular section and fluidly connected (or linked) together and connected to static mixers and tanks or reservoirs.

Preferably, the apparatus and the method according to the invention are dedicated to the recovery and to the purification from cells, of extra-chromosomal nucleic acids sequence(s), such as DNA plasmid(s) that will be purified from cells impurities (or contaminants), especially from *E. coli* contaminants, such as host cells proteins, RNA sequences, genomic DNA sequences, endotoxins, . . . .

The apparatus used in the method according to the invention comprises or consists of several units that are fluidly connected and include a preparation unit 1, a cells lysis unit 20, a neutralization unit 30, optionally a precipitation unit 40, a separation (decantation or clarification) unit 50, an injection unit 70 and a filtration unit.

Furthermore, the cells lysis unit 20 could be fluidly connected to a production unit (including a reaction tank not represented in the figures), but used for the growth and multiplication of cells comprising the extra-chromosomal nucleic acids sequence(s) of interest to be recovered.

In the passageway of the apparatus according to the invention the flow rates follow-up is obtained by chronometers, weight monitoring and/or by flow meters added to the different tubing(s) and connections between tubing(s) are of the "Y type"

The first part of the apparatus according to the invention, is a preparation unit 1 which can present two different formats. According to a first embodiment, not presented in the figures, the apparatus according to the invention contains a lysis medium tank or reservoir with the (alkaline) lysis medium connected by a first tubing and a pump and possibly a flowmeter, to the lysis unit 20 to mix the cells with the added (alkaline) lysis medium.

According to another embodiment of the present invention and as presented in the figures, the preparation unit 1 is advantageously made of at least two separate tanks (2 and 3), both maintained at room temperature, the first tank 2 containing NaOH (RM2-A) and the second tank 3 containing one or more detergents (RM2-B), preferably Sodium Dodecyl Sulfate (SDS).

Both tanks 2 and 3 are in fluid connection respectively to a first set of tubing elements 4 and 5, preferably via a first pump 6 and a second pump 7, wherein these pumps (6 and 7) are controlling the adequate added amounts of each reactive product (NaOH, detergent and possibly one or more other molecule(s)) are mixed and fed to a first static mixer 9 to form the lysis solution.

The reactive compounds present in the tubings of the first tubings set (4 and 5) meet in a "Y type" connection and are pushed, via an inlet or opening 8 into the first static mixer 9 used for the efficient homogeneous mixing of all the introduced compounds, to form the lysis buffer (RM2 buffer medium). This mixing insures the stability and constant composition quality of the (alkaline) lysis medium. A homogeneous mixing means a mixing that is homogeneous according to the naked human eye.

The outlet or exit 10 of this first static mixer 9 of the preparation unit 1 is in fluid connection, via a second tubing 11 to the inlet or opening 21 of a second static mixer 22 which is part of the cells lysis unit 20. Preferably, the second static mixer 22 of the cells lysis unit 20 comprises between 12 and 24 mixing elements, preferably 18 mixing elements.

The cells lysis unit 20 is the passageway described above and preferably includes the second static mixer 22, which is in fluid connection by a "Y-Type" connection at its inlet 21, to both the second tubing 11 of the preparation unit 1 and, via a third tubing 23 and a pump 24, to a cells suspension tank 25 containing at a suitable temperature, preferably at a temperature comprised between about 2° C. and about 8° C., the suspended cells with the extra-chromosomal nucleic acids sequence(s) to recover.

The lysis or the cells disintegration is performed by addition of the cells lysis buffer, being preferably a mixture of NaOH+SDS, from the first static mixer 9 and the suspended cells from the cell suspension tank 25 to the second static mixer 22. Although the generated solution of disintegrated cells is viscous, an efficient homogenization was obtained without degrading the plasmid.

The inventors have optimized the tubing diameter and lengths and the pump output in order to assess the optimal mean contact time of the cells and the lysis buffer. The apparatus that they developed allows surprisingly short mean contact times, such as less than 5 minutes preferably between (about) 1 minute and (about) 5 minutes, more preferably (about) 2 minutes, which advantageously prevents the degradation of the extra-chromosomal nucleic acids sequence(s) of interest, preferably the DNA plasmid.

The outlet or exit 26 of this second static mixer 22 is in fluid connection to the features of the neutralization unit 30, via a fourth tubing 27 having an adequate length and diameter allowing to obtain the optimal contact time for the recovering of the cells lysate.

The neutralization unit 30 comprises a neutralization tank 31 containing a neutralization medium (RM3), preferably made of a solution of acetic acid and acetate, preferably maintained at a pH comprised between about 5.0 and about 6.0 preferably of about 5.5 and consisting of 3M of acetate and 15% (v:v) of acetic acid, preferably used at a temperature comprised between 2° C. and 8° C., preferably of about 4° C.

This neutralization tank 31 is in fluid connection, via a fifth tubing 32 and via a pump 33, to an inlet or opening 34 of a third static mixer 35. The neutralization medium can be cooled before use by storage of the neutralization tank 31 in a cold room for a sufficient amount of time, or cooled down in a continuous manner from room temperature (comprised between 20° C. and 25° C.) to a lower temperature comprised between 2° C. and 8° C., preferably of about 4° C., by a cryostat 36 and a heat exchanger 39 surrounding a section of the fifth tubing 32.

The inlet or opening 34 of this third static mixer 35 is also I fluid connection to the fourth tubing 27 providing the cells lysate. Preferably, this third static mixer 35 comprises between 6 and 16 mixing elements, preferably 10 mixing elements.

The inlet 34 of this third static mixer 35 is preferably in fluid connection by a "Y-type" connection to the two tubing elements 32 and 27, so that both fluids flows are sent to the static mixer 35 to obtain a rapid and efficient neutralization of the cells lysate to stop the lysis reaction and to form a neutralized cells lysate.

The inventors have further optimized the tubing diameter and length, and the pump output in order to assess the optimal mean contact time of the lysed cells under neutralization. The apparatus developed allows short mean contact time, such as less than 3 minutes, preferably of (about) 0.5 minute to (about) 3 minutes, more preferably (about) 1 minute, which advantageously leads to an efficient neutralization of the lysed cells before the addition of the precipitation agent.

The outlet or exit 37 of this third static mixer 35 is in fluid connection to a sixth tubing 38 collecting the obtained neutralized lysate mixture. The sixth tubing 38 can be directed and is in fluid connection to the inlet or opening 45 of a fourth static mixer 41 forming part of the precipitation unit 40.

The inlet or opening 45 of the fourth static mixer 41, is also in fluid connection to a seventh tubing 42, via a pump 43, to a divalent salt(s) solution tank 44 comprising a solution of divalent ions salt(s) (RM4), preferably hydrated calcium chloride.

Again, a "Y-type" connection is preferably used between both tubings 38 and 42, so that both fluids flows are sent to the fourth static mixer 41 to obtain a rapid and efficient mixing. A solution of divalent salt(s) pumped from the tank 44, via the seventh tubing 42 to the inlet 45 of the fourth static mixer 41, is added continuously to the neutralized cells lysate added into the fourth static mixer 41 from the sixth tubing 38 to obtain a cell lysate mixture. This fourth static mixer 41 insures a thorough mixing of the dense and viscous solutions and improves the precipitation reaction. However, others means than this static mixers, including means for generating a Venturi effect, can be used for the efficient mixing of fluids, including the dense and viscous divalent salt(s) solution obtained from the tank 44.

This fourth static mixer 41 comprises between 4 mixing elements and 18 mixing elements, preferably only 4 mixing elements. An optimum number of 10 mixing elements could be selected for an efficient mixing of the salts and the neutralized lysed cells to obtain the cells lysate mixture. However, as a higher number of mixing elements will produce smaller particles and precipitate, which are less easily eliminated from the soluble fraction during separation (decantation or clarification) and would reduce the production and purification yield and increase purification time.

The outlet or exit 46 of the fourth static mixer 41 is in fluid connection, via an eighth tubing 47 to a separation tank 51 of the separation unit 50. The cells lysate mixture 52 is supplied to this separation tank 51 from the fourth static mixer 41. It will be convenient to note that the fourth static mixer 41 is optional, and tubing 38 can be directly fed to separation tank 51 of the separation (or decantation or clarification) unit 50.

In the apparatus according to the invention, the separation unit 50 is used for separation, decantation or clarification of a cells lysate mixture 52 from the sequence(s) of interest from impurities (or contaminants) and is improving the yield, especially the delay and the efficiency of separation, decantation or clarification and improving recovery of the extra-chromosomal nucleic acids sequence(s) of interest from this cells lysate mixture 52.

Figure 2:
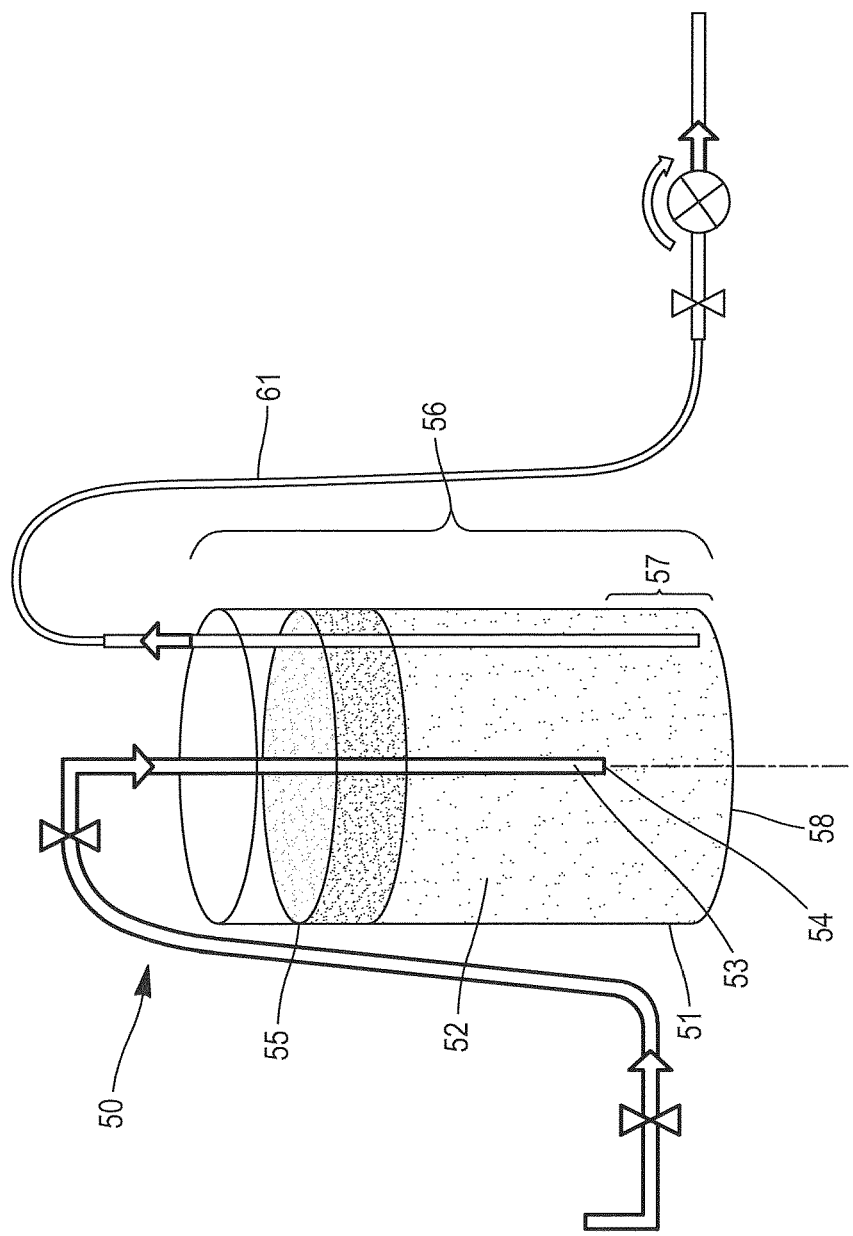
FIGS. 2 and 3 represent different configurations of the separation unit of the apparatus according to the invention.
Figure 3:
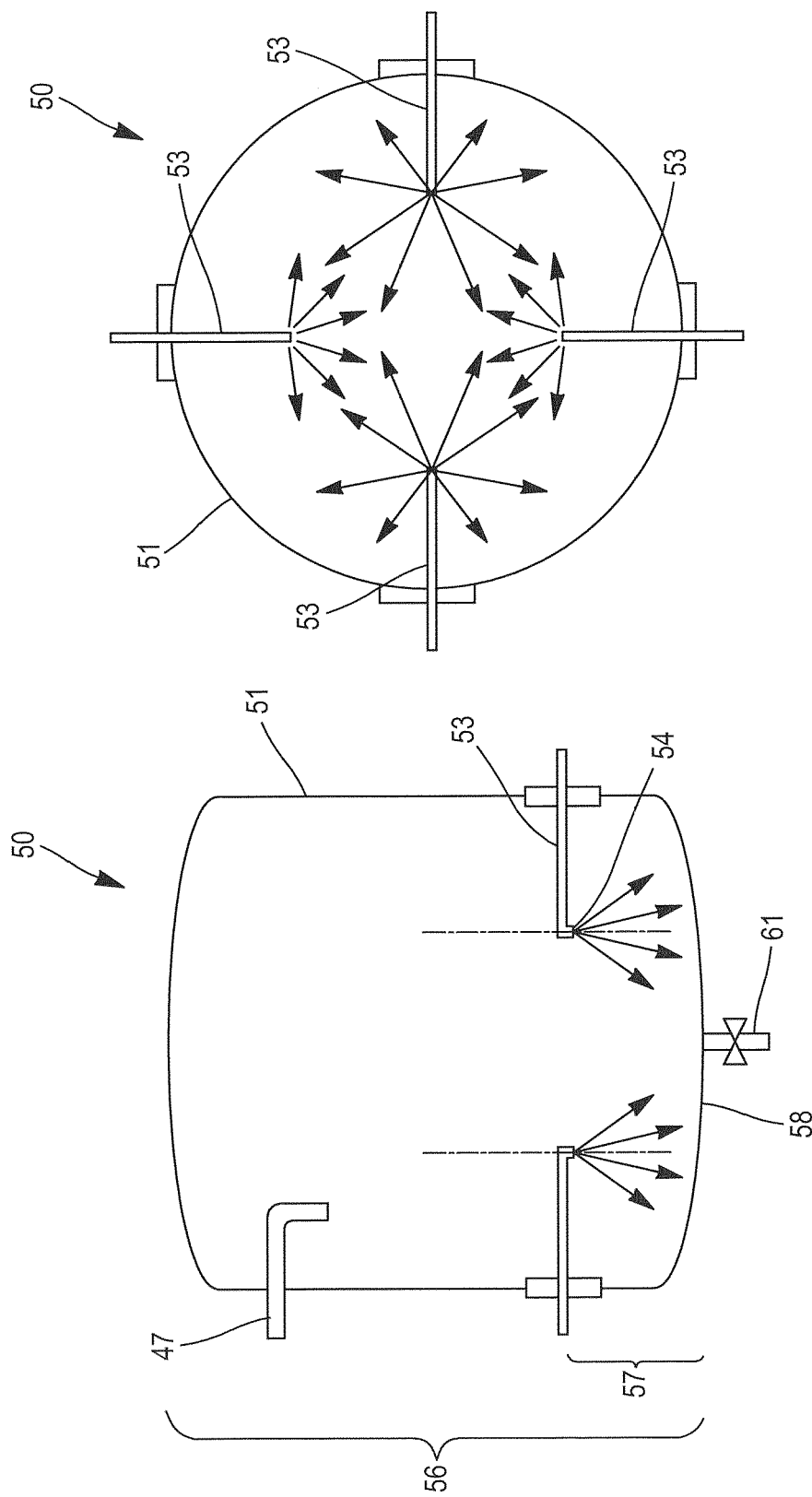
Figure 4:
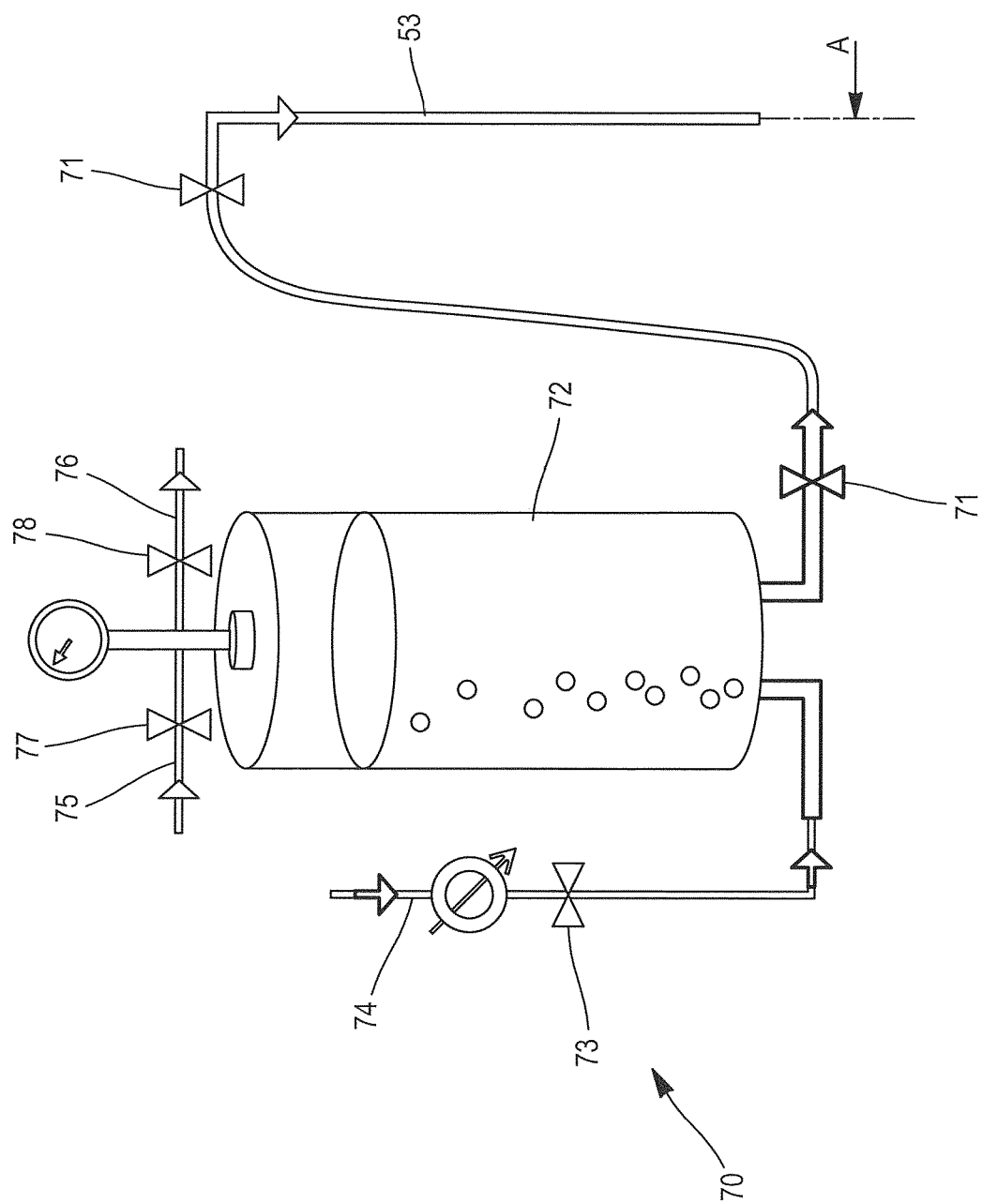
FIG. 4 represents the injection unit connected to the separation unit of the apparatus according to the invention.

The separation unit 50 represented in FIGS. 2 and 3 is connected to an injection (floatation) unit 70 represented in FIG. 4 and allowing injection inside the separation tank 51, of a liquid aqueous medium more preferably water, comprising large amounts of a dissolved gas being preferably air, nitrogen, $CO_2$, oxygen or ozone, more preferably air into the separation tank 51. This liquid aqueous medium is maintained at room temperature with the gas, preferably air, and introduced at a suitable pressure, preferably a pressure of at least 2 barg.

The separation, decantation or clarification is efficiently improved by means of an injection of this liquid aqueous medium, preferably water comprising saturated or near-saturated levels of the dissolved gas, preferably selected from the group consisting of air, $CO_2$ or nitrogen, or a mixture thereof, via one or more injection pipe(s) 53 having an exit 54, possibly comprising a nozzle into the cells lysate mixture 52 present in the separation tank 51. The exit 54 of this injection pipe 53 is disposed in the direction opposite to the surface 55 of the cells lysate mixture 52 present in the separation tank 51 and towards or in the direction of the bottom surface 58 of the separation tank 51.

As represented in FIG. 3, the configuration of the decantation unit 50 may include a separation tank 51 wherein more than one injection pipe(s) 53 are introduced, preferably two, three or four injection pipes 53, possibly arranged at diagonally opposite positions in the separation tank 51, preferably with an exit 54 of each injection pipe 53 being disposed in the same plane parallel to the plane formed by the bottom of the separation tank 51 and advantageously at equivalent distance from each other and from the sides and bottom of the decantation tank. In FIG. 3 four injection pipes 53 are represented at diametrically or diagonally opposite positions.

As represented in the FIG. 3, the exit 54 of each injection pipe 53 is disposed facing away from the top surface 55 of the cells lysate mixture 52 present in the separation tank 51 and this exit 54 is facing the tank bottom surface 58, but oriented to inject the liquid aqueous medium vertically downwards the direction of this bottom surface 58. This configuration avoids the formation of important convection movement in the cells lysate and avoids the dispersion of the precipitates or flocs from the top precipitate layer.

In the separation unit 50 of the apparatus according to the invention, the cells lysate mixture 52 is introduced by the eighth tubing 47 disposed along the side wall of the separation tank 51 and fills partially the separation tank 51. There should remain a free volume in this separation tank 51 sufficient to handle the addition of the liquid aqueous medium saturated with gas under pressure.

The exit 54 of the injection pipe(s) 53 is advantageously positioned at a height 57 from the bottom of the separation tank 51 between ⅙ and ⅚ of the height 56 of this separation tank 51, more advantageously positioned at a height 57 from the bottom of the separation tank 51 between ¼ and ¾.

The injection pipe 53 may present a nozzle exit 54, with a narrow exit. Advantageously the injection pipe 53 presents a ratio between its internal diameter and the diameter of its nozzle exit 54, which is higher than or equal to (about) 2, more preferably higher than or equal to (about) 3, and may be lower than or equal to 50. This configuration and ratio between the internal diameter pipe size and its nozzle exit ensure that the depressurization of the liquid aqueous medium only starts at the nozzle itself, and not within the injection tubing 53. By so doing, the liquid aqueous medium with the dissolved gas is kept at a suitable elevated pressure up to the exit nozzle, so that pressure drops at the nozzle exit only. However, in specific configuration of the apparatus of the invention allowing production of lower amounts of extra-chromosomal nucleic acids sequence(s) of interest, this ratio is of (about) 1 or near the value of 1 with an injection pipe 53 that neither include a nozzle and nor a reduction of the exit 54 diameter. As a result, a rapid and efficient separation, clarification or decantation of the cells lysate mixture 52 from its contaminants or impurities, which are dispersed in the separation tank 51 can be obtained. The contaminants or impurities will float at the top surface 55 of the cells lysate mixture 52. Preferably, this separation duration is comprised between (about) 5 minutes and (about) 3 hours, but could be applied for longer periods of up to 1 or 2 days.

As represented in FIG. 4, the added liquid aqueous medium containing the dissolved gas is obtained from the injection pipe 53 which is connected, preferably through a valve 71 to the injection or floatation unit 70.

The injection (or floatation) unit 70 comprises a tank 72 containing a liquid aqueous medium, preferably water. This liquid aqueous medium tank 72 comprises an inlet, advantageously arranged in a lower part of the tank 72, which is connected, preferably via a valve 73 to a tubing element 74 of a bubbling device, supplying in the liquid aqueous medium tank 72 a gas, preferably air. Additional tubing elements (75 and 76) and valves (77 and 78) for a gas (air) introduction and expulsion can be connected to the aqueous medium tank 72.

The liquid aqueous medium tank 72 is advantageously a closed vessel arranged to hold a liquid under suitable elevated pressure. The separation (or decantation) tank 51 is advantageously configured to hold the cells lysate mixture 52 at substantially atmospheric pressure.

The liquid aqueous medium is enriched and advantageously saturated with the dissolved gas under pressure, by a bubbling of the pressurized gas obtained from the bubbling device into the liquid aqueous medium. By so doing, this liquid aqueous medium is enriched in the dissolved gas (Henry's law). Advantageously, the bubbling is performed for a sufficient amount of time to reach the complete saturation. The pressure in the liquid aqueous medium tank 72 is advantageously kept constant during the bubbling, at a value of 2 barg or more, preferably between 2 barg and 50 barg, more preferably between 3 barg and 25 barg.

The liquid aqueous medium enriched in dissolved gas is injected in the separation tank 51 advantageously during a period comprised between a few seconds and a few minutes, preferably between 5 seconds and minutes. Preferably, in the method and apparatus according to the invention, the volume % of the injected liquid aqueous medium is comprised between 0.2% and 25% (v/v), preferably comprised between 0.5% and 15%, more preferably comprised between 1% and 10%, compared to the volume of the (decanted) cells lysate mixture.

Referring again to FIGS. 2 and 3, the separation tank 51, further includes a collecting tubing 61 for recovering the soluble fraction or clarified phase containing the extra-chromosomal nucleic acids sequence(s) of interest, from the cells lysate mixture 52 present into the separation tank 51.

The inlet of the collecting tubing 61 is advantageously disposed at the bottom of the separation tank 51 for obtaining an efficient pumping of the soluble fraction or clarified phase with minimising liquid movements in the separation tank 51 to avoid a re-suspension of the contaminants or impurities precipitates. Tubing 61 advantageously removes the soluble fraction from separation tank 51 in the bottom part 57, below the level of exit 54 of injection pipe 53. Tubing 61 can be connected to a filtration unit.

A further purification with known means (such as filters, chromatographic columns and collecting tanks) and method steps well known by the skilled person can also be performed.

Figure 5:
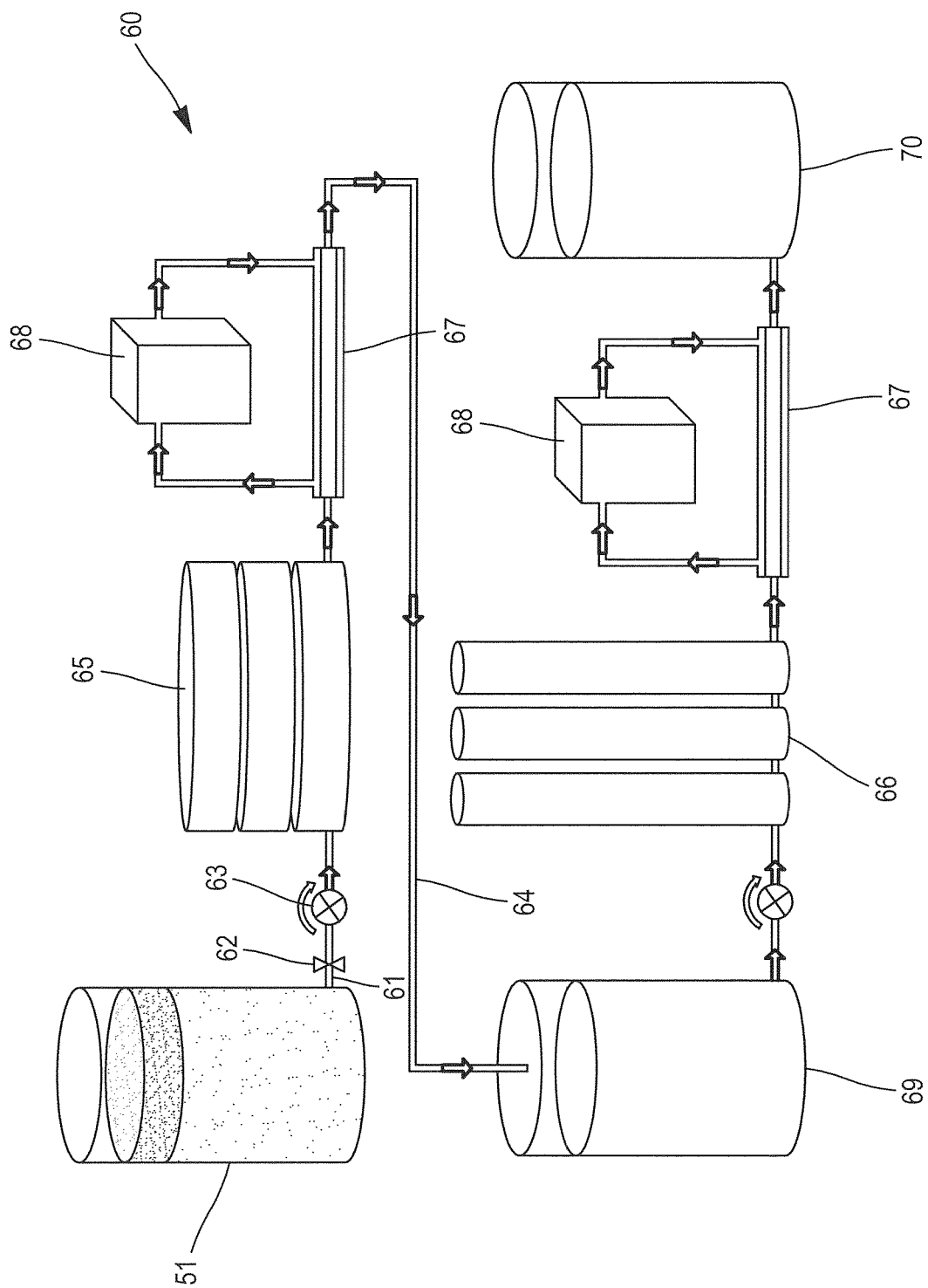
FIG. 5 represents a filtration unit connected to the separation unit of the apparatus according to the invention.

As represented in FIG. 5, the flow of this soluble fraction or clarified phase of the cells lysate mixture, outside the separation tank 51 is advantageously obtained through the opening of a valve 62 and a pump 63 connected to another section of a tubing element 64 allowing the flow of the soluble fraction or clarified phase of the cells lysate mixture towards another filtration unit 60 for its further purification with methods steps well known by the skilled person. This filtration unit can comprise one or more filters 65 and 66 and/or one or more chromatographic columns with suitable elution material. Furthermore during filtration, ultrafiltration and/or diafiltration, one or more tubing section(s), especially section(s) of the tubing element 64 could be surrounded by a heat exchange device 67 connected to a cryostat 68 for a cooling of the filtrated and clarified lysate to a temperature as closed to 4° C. as possible (in the rage of 2° C. to 8° C.) preferably a temperature that can be maintained for an adequate time (overnight) in suitable (and possibly refrigerated) tank 69.

In the apparatus and method according to the invention, the tubing elements may include flow meters or other devices for controlling the introduction of suitable volumes (per unit of time) of the different fluids necessary for the lysis system, the tanks or reservoirs. The apparatus may also include weight monitoring elements, such as weight balances of the different tanks or reservoirs to measure the amount of introduced solution or active compounds (lysis solution, neutralization solution, cells in suspension, liquid aqueous medium saturated in gas under pressure) at each step of the method according to the invention. Conditions and efficiency of purification obtained by the apparatus and the method of the invention are summarized in the following table 1 which presents an overview of possible process conditions.

TABLE 1

| | |
|---|---|
| Liquid aqueous medium temperature | 4° C. to room temperature (the air dissolves much slower at 4° C.) |
| Air pressure | 6 barg |
| Compressed gas bubbling in the aqueous medium duration | >=1 minutes |
| Lysate volume treated | From almost nothing (less than 1 liter) up to cubic meters (3 × 1500 L planned for the Step2 capacity expansion at KEGT), depending on the injection system. |
| Liquid aqueous medium volume (% v/v) | From 0.5 to 20% per injection, successive injections improving the floatation effect |
| Liquid aqueous medium injection duration | From 5 seconds to 5 minutes depending on the injection flow rate and injected volume. |
| Floatation duration | Between 5 min and 3 hours, typically 15-30 min between each injection or before collection. |
| Full process duration | From cells lysis to final 0.2 μm filtration: less than around 8 hours at any scale. |
| separation efficiency | Volume of clear lysate recovered/total volume (lysate + precipitates layer): By gravimetric decanting: 70% to 75% recovery With floatation: 85% to 90% recovery ⇒ 10 to 15% volume recovery gain |
| Turbidimetry reduction | By gravimetric decanting: about 50 NTU With floatation: <20 NTU ⇒ More than 2x turbidimetry reduction ⇒ Depth filtration membrane area needed decreased by about the same factor. |

The advantages brought by the new process and apparatus of the invention are numerous. It is a simple and robust, efficient, reproducible and automatable process and apparatus (or plant) can be used.

A goal of the process and apparatus according to the invention is to keep separation duration very low, preferably at a maximum of two hours. This goal was reached and even exceeded, the full separation being obtained after only about 1 hour or even lower time.

Another goal is to obtain a robust separation (decantation or clarification) where, for each run, almost no particles were left on the bottom of the separation tank (51) or dispersed in the cells lysate mixture, as they quickly clog the clarification depth filters and should not be pumped. This goal is reached as almost all particles are floating on the top of the separation (decantation or clarification) tank 51 after the floatation, and even exceeded as the clarified fraction of the lysate is much clearer (decreased turbidity) than with a classical gravimetric separation step. As a consequence, less depth filters surface is needed for separation, which means lower costs, wastes, space needed in the zone, handling, etc.

An additional goal is to enhance the recovery of the (total) soluble fraction or clarified phase, and is also reached as the soluble fraction or clarified phase lost in the precipitates layer is now replaced by a gas, such as air, this precipitates layer floating above this soluble fraction or clarified phase instead of being immersed in it. The volume of recovered soluble fraction or clarified phase has therefore been increased by 10% to 15%.

A further goal of the new process and apparatus of the invention is the treatment of large amounts of cells pellets, preferably by increasing the flow rates, while keeping at least the same process duration time (lower than about 4 hours) for every scale and to obtain the recovery of large amounts (kgs) of purified extra-chromosomal nucleic acids sequence(s) of interest.

The inventors have also tested the direct injection of gas bubbles, instead of the liquid aqueous medium comprising the dissolved gas into the cells lysate mixture contained in the separation tank 51. However, the injection of gas bubbles generates down to up movements due to bubble rising to the top, and therefore a mixing of the soluble fraction with the precipitate layer, containing impurities and contaminants of the extra-chromosomal nucleic acids sequence(s) to be recovered from the cells lysate mixture. This mixing and introduction of flocs and others solid particles, including contaminants of the extra-chromosomal nucleic acids sequence(s) to recovered in the soluble fraction or clarified phase, will reduce the efficiency of this soluble fraction recovery and also the extra-chromosomal nucleic acids sequence(s) purification.

On the other side, in the method and apparatus according to the invention, the injection of the liquid aqueous medium comprising dissolved gas into the cells lysate mixture, allows advantageously a complete or almost complete recovery of the soluble fraction or clarified phase that is not, or almost not contaminated by the precipitate layer made of flocs floating above the soluble fraction of the cells lysate mixture.

In addition, the method and apparatus according to the invention does not contain gas injection frit or other microporous material that would be necessary to reduce the bubbles sizes, such devices being very prone to be clogged by the precipitated particles and also being an important source of cross-contaminations from batch to batch due to their poor cleanability. The design of the method and apparatus according to the invention allows after the soluble fraction (or clarified phase) of the cells lysate recovery, a rapid and efficient subsequent washing of the separation (decantation or clarification) means, especially the separation tank 51 for its further use, possibly through injection of washing liquid(s) from the injection pipe 53 or from others tubing elements into this separation tank 51.

After lysis, the precipitates have a density similar to the liquid phase (soluble fraction or clarified phase) of the cells lysate. Still, they often tend to rise very slowly to the top of the separation tank due to a few microbubbles sticking to them, which are coming from small amounts of gas dissolved in the starting reagents. The addition of gas bubbles as proposed in the state of the art publication, in continuous during the lysis process is a way to increase the amount of bubbles to help this floatation effect. On the other hand, in the method of the state of the art, the binding strength of the bubbles to the precipitates is very low, so mixing movements or agitation easily unsticks the bubbles from the precipitates, breaking the floatation effect and making them sink again.

At the exit of a continuous lysis system, the lysate must be sent to a separation tank, where the precipitate made of flocs 101 or particles 100 (made of the impurities of the sequences(s) of interest to be recovered) are separated from the soluble fraction. If the cells lysate is sent to the bottom (exit immersed into the cells lysate) and if gas bubbles are added in continuous during the lysis, as proposed in the state of the art, those gas bubbles will quickly go up right above the exit (like an air pump in an aquarium) and will produce an upward stream within the cells lysate, leading to mixing movements preventing the precipitates to settle at the top of the separation tank correctly. If the cell lysate is sent to the top of the separation tank, it will also create mixing movements within the top layer of particles 100 that have already started to float and will push them back into the solution, breaking part of the floatation effect. These mixing movements are one of the drawbacks of the state of the art requiring continuous addition of bubbles during the lysis process. Another drawback comes from the continuous nature of the treatment. New cells lysate with precipitates and bubbles are added continuously to the separation tank that already contains the cells lysate previously generated and which has already started to settle. This leads to treatment heterogeneity in the separation tank.

Figure 6:
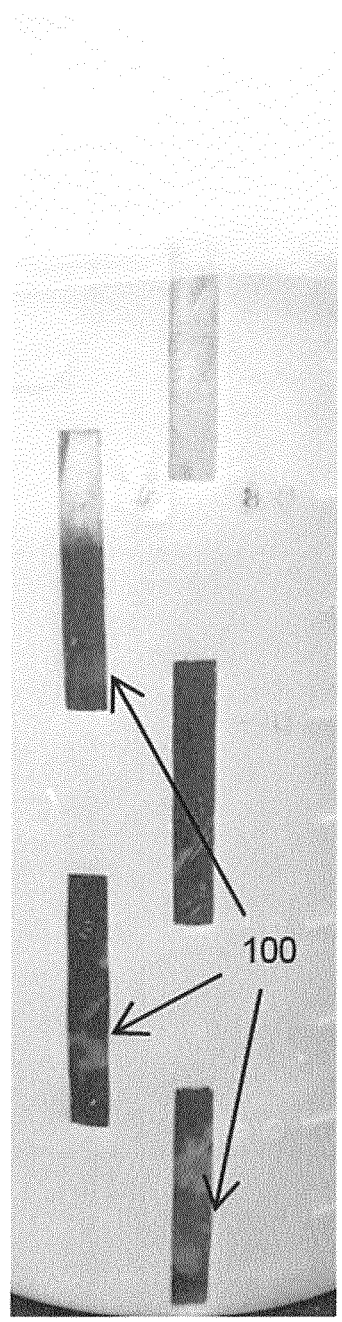
FIG. 6 represents separation results obtained with methods and the apparatus of the state of the art.
Figure 7:
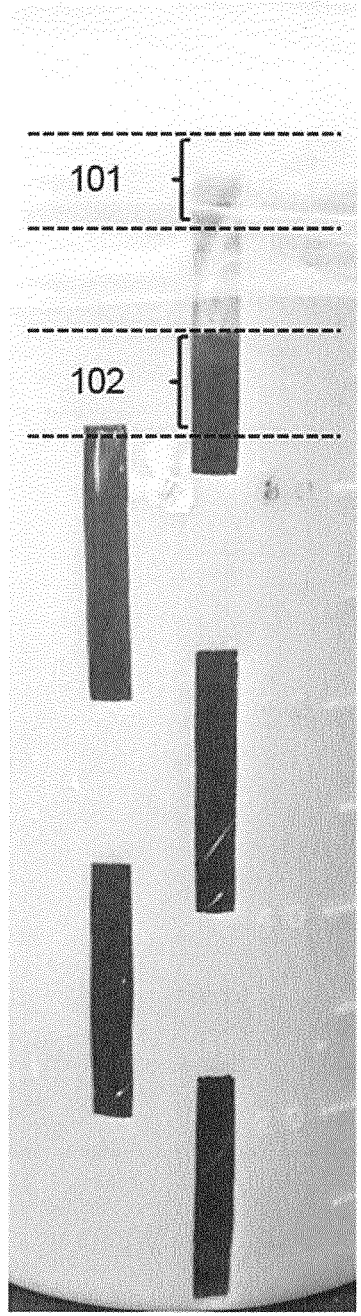
FIG. 7 represents separation results obtained with the method and apparatus according to the invention.

The present invention brings a solution to avoid these mixing movements and treatment heterogeneity by performing the floatation in "a static manner", when the lysis is finished and the separation tank 51 is filled. Injecting the liquid aqueous medium with the dissolved gas under pressure allows the treatment of the whole cells lysate volume at the same time. As a liquid is injected instead of a gas, it quickly mixes to the whole volume to treat. Right after injection, due to the fact that the separation tank is at atmospheric pressure, the gas that was dissolved in the liquid medium under pressure (i.e. in a liquid phase) turns back into the gaseous phase, mainly in contact with the particles playing the role of nucleation centers. Therefore, the microbubbles stick to the precipitates and all particles rise at the same time in a linear way to the top of the separation tank 51, pushing each other in the same direction. This creates a strong plunger effect: the particles being above are pushed further out of the soluble fraction of the cells lysate by the ones being below. This plunger effect leads to much higher separation efficiency. After treatment, most of the particles have not only been separated at the top of the separation tank 51, but also pushed out of the liquid phase or Gas coming from the injection of the liquid medium saturated with a dissolved gas, will replace the liquid cell lysate that was previous entrapped in the spaces between the particles and push the precipitate layer (101), thus significantly increasing the recovery yield, as shown in the following table 2 and within the comparative FIGS. 6 and 7 (see volume gain 102 with the applied floatation method of the invention and remaining particles 100 obtained with the applied gravimetric method of the state of the art).

Finally, the present invention is designed in such a way that succeeding injections of the aqueous liquid medium with the dissolved gas under pressure is performed without dispersing again the particles that have been separated. Each succeeding injection decrease the amount of micro-particles left in cell lysate and eases clarification

TABLE 2

|  | Gravimetric | Floatation |
|---|---|---|
| Volume recovery | 70-75% | 85-90% |

The invention claimed is:

1. A method for obtaining one or more extra-chromosomal nucleic acids from cells and comprising the steps of:
   a) optionally cultivating cells comprising the extra-chromosomal nucleic acids of interest,
   b) disintegrating the cells by mixing the cells in suspension with a lysis medium to form lysed cells, c) neutralizing the lysed cells by adding a neutralization solution to said lysed cells to produce a first cells lysate mixture comprising a soluble fraction and a precipitate, d) optionally further precipitating contaminants away from the extra-chromosomal nucleic acids of interest to obtain a second cells lysate mixture, by mixing the first cells lysate mixture with a solution containing one or more salt(s), wherein the salt(s) comprise one or more of $CaCl_2$), $MgCl_2$, $ZnCl_2$, $SrCl_2$, $BaCl_2$, LiCl, ammonium acetate, ammonium sulfate, sodium sulfate and magnesium sulfate, e) collecting the cells lysate mixture obtained from step c) or from step d), f) separating the soluble fraction comprising the extra-chromosomal nucleic acids of interest of the cells lysate mixture from the precipitate in a separation tank, and g) recovering the separated soluble fraction comprising the extra-chromosomal nucleic acids of interest, wherein the separation step f) consists of dissolving a gas in a liquid aqueous medium under a pressure higher than atmospheric pressure followed by injecting the liquid aqueous medium comprising the dissolved gas into the cells lysate mixture contained in the separation tank.

2. The method of claim 1, wherein the gas is dissolved in the liquid aqueous medium by gas bubbling under pressure of at least 2 barg.

3. The method of claim 1, wherein the liquid aqueous medium comprising the dissolved gas is injected into the cells lysate mixture in a volume amount of between 0.2% and 25% v/v, relative to the volume of the cells lysate mixture.

4. The method of claim 1, wherein the liquid aqueous medium comprising the dissolved gas is injected into the cells lysate mixture under a pressure of at least 2 barg and wherein the cells lysate mixture is at atmospheric pressure in the separation tank.

5. The method of claim 1, wherein the liquid aqueous medium comprising the dissolved gas injected into the cells lysate mixture is saturated with the gas.

6. The method of claim 1, wherein the liquid aqueous medium comprising the dissolved gas is injected downwards towards the bottom of the separation tank.

7. The method of claim 1, wherein the injection of the liquid aqueous medium comprising a dissolved gas is a single injection or is successive injection.

8. The method of claim 1, wherein the neutralization of lysed cells from step c) with a neutralization solution is done by a static mixer having a mixing linear speed equal to or higher than 100 cm/min.

9. The method of claim 1, wherein the lysis medium is a mixture of NaOH and a detergent.

10. The method of claim 1, wherein the liquid aqueous medium comprising the dissolved gas is injected into the cells lysate mixture in a volume amount of between 0.5% and 15% v/v, relative to the volume of the cells lysate mixture.

11. The method of claim 9, wherein the detergent comprises Sodium Dodecyl Sulfate (SDS).

12. An apparatus for carrying out the method of claim 1 to obtain one or more extrachromosomal nucleic acids of interest from cells, the apparatus comprising:

a preparation unit comprising one or more tanks configured to contain constituents of a lysis medium and comprising an outlet, a cells lysis unit comprising a cells suspension tank configured to contain cells with the extra-chromosomal nucleic acids of interest, and further comprising an inlet and an outlet, wherein the inlet is fluidly connected to the cells suspension tank and with the outlet of the preparation unit, a neutralization unit configured to generate a first cells lysate mixture, the neutralization unit comprising a neutralization solution tank, an inlet and an outlet, wherein the inlet is in fluid connection to the neutralization solution tank and with the outlet of the cells lysis unit, optionally a precipitation unit configured to obtain a second cells lysate mixture, the precipitation unit comprising a divalent ion salt(s) solution tank, an inlet and an outlet, wherein the precipitation unit inlet is in fluid communication with the outlet of the neutralization unit to receive the first cells lysate mixture, a separation unit configured to collect the cells lysate mixture, the separation unit comprising a separation tank having an inlet fluidly connected to the outlet of the neutralization unit or the outlet of the precipitation unit, and an injection unit configured to inject a liquid aqueous medium comprising a dissolved gas into the separation tank, the injection unit comprising a liquid aqueous medium tank and a bubbling device configured to bubble a gas to be dissolved into the liquid aqueous medium tank, at a pressure higher than atmospheric pressure.

13. The apparatus of claim 12, wherein the injection unit comprises one or more injection pipe(s) having an exit disposed towards a bottom surface of the separation tank.

14. The apparatus of claim 13, wherein the one or more injection pipe(s) is (are) disposed to inject the liquid aqueous medium into the separation tank at a height located between ⅙ and ⅝ of the total height of the separation tank from the tank bottom.

15. The apparatus according to claim 12, wherein the bubbling device is configured to inject a gas to be dissolved into the liquid aqueous medium tank, at a pressure higher than or equal to 2 barg.

16. The apparatus according to claim 15, wherein the bubbling device is configured to keep the liquid aqueous medium tank under a pressure of at least 2 barg.

17. The apparatus according to claim 12, wherein the injection unit is configured to inject the liquid aqueous medium having the dissolved gas intermittently into the separation tank.

18. The apparatus of claim 12, wherein the preparation unit, the cells lysis unit, the neutralization unit and/or the precipitation unit comprise(s) one or more static mixer(s).

19. The apparatus of claim 13, wherein the one or more injection pipe comprises an exit nozzle and wherein the ratio between the injection pipe internal diameter and exit nozzle diameter is at least 2.

* * * * *